United States Patent [19]
Dohring et al.

[11] 3,939,841
[45] Feb. 24, 1976

[54] ACUPUNCTURE NEEDLE GUIDE AND RESTRAINT

[76] Inventors: Albert A. Dohring; Grace H. Dohring, both of 24028 Union, Dearborn, Mich. 48124

[22] Filed: Mar. 6, 1974

[21] Appl. No.: 448,618

[52] U.S. Cl..... 128/303.19; 128/2.1 C; 128/303.18; 128/329 A
[51] Int. Cl.² ......................................... A61H 39/08
[58] Field of Search .......... 128/2.1 C, 2.1 R, 329 A, 128/303 B, 303.18, 303.19, 215, 221; 403/104, 109; 279/79, 96, 102; 269/254 CS

[56] References Cited
UNITED STATES PATENTS

| | | | |
|---|---|---|---|
| 859,724 | 7/1907 | Barr | 128/215 |
| 1,279,302 | 9/1918 | Dunlap | 279/79 |
| 1,384,355 | 7/1921 | Smith | 128/221 |
| 1,524,242 | 1/1925 | Hein | 128/221 |
| 1,774,707 | 9/1930 | Gau | 128/221 |
| 1,792,120 | 2/1931 | Pieper | 279/102 |
| 1,814,274 | 7/1931 | Williamson | 279/79 |
| 1,821,079 | 9/1931 | Schultze | 279/79 |
| 3,147,750 | 9/1964 | Fry | 128/221 |
| 3,460,537 | 8/1969 | Zeis | 128/303 B |

OTHER PUBLICATIONS
Stillings, "Acupunc. . . . Ancient Chinese Method of Healing," J.A.A.M.I., Vol. 7, No. 1, Jan., Feb., 1973, p. 16.

Primary Examiner—Robert W. Michell
Assistant Examiner—Lee S. Cohen
Attorney, Agent, or Firm—Allan J. Murray

[57] ABSTRACT

A locating device for transmitting a mild electrical direct current or pulsating direct current through the body of a patient to locate through increased resistance, as indicated on the meter, areas in the body that may benefit from the application of an acupuncture needle. The locating device has an elongated handle with the necessary electrical connection. At one end portion of the handle a transversely formed hole receives an elongated, tubular, electrically conductive needle support and guide. Acupuncture needles are very thin and flexible, and require support to obtain best usage thereof. A restraint, formed of a resiliently yieldable strip of metal or wire extends across one end of the tubular guide and is disposed thereon to frictionally engage a needle to resist travel of the needle downwardly through the tubular guide. Acupuncture needles are formed with a head substantially thicker than the needle itself, and the aforesaid restraint is sufficiently yieldable to afford passage of the head past the wire and downwardly into the tube where desired. A spring is provided to yieldably retain the tubular guide in a predetermined position relative to the longitudinal axis of the handle, and further means is provided to apply a more positive resistance to dislodgement of the tubular guide from a predetermined position.

6 Claims, 9 Drawing Figures

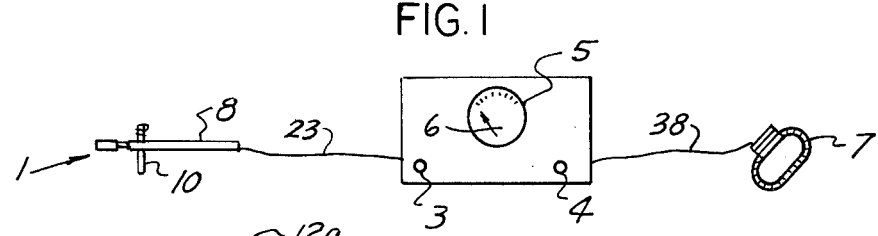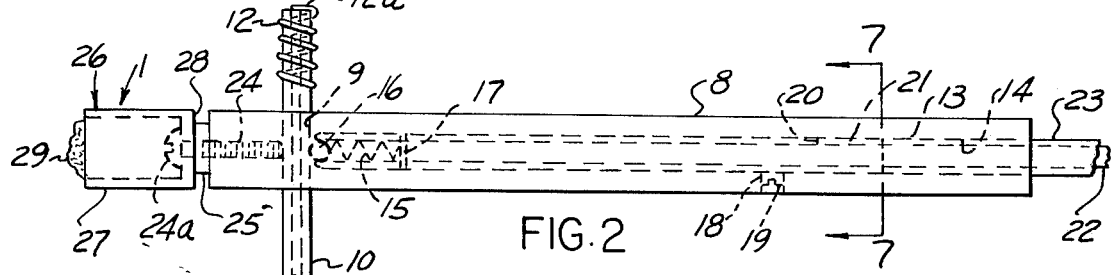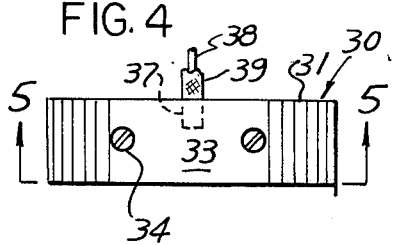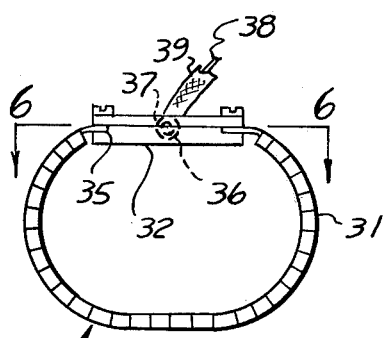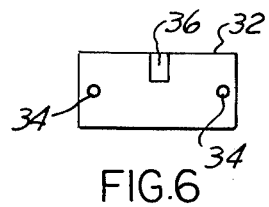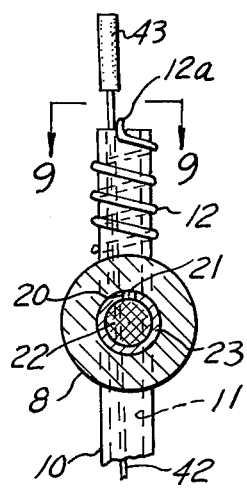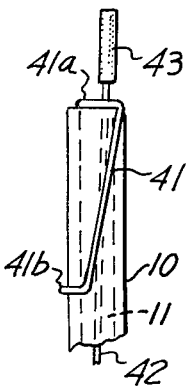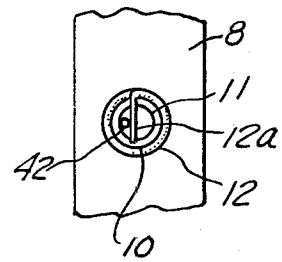

ACUPUNCTURE NEEDLE GUIDE AND RESTRAINT

FIELD OF INVENTION

The field of invention is that of devices for locating areas in the body of a patient which would benefit from acupuncture therapy, with a subsequent employment of an acupuncture needle in the area located, and electrical therapy, if needed.

BACKGROUND OF INVENTION

This invention is related to that disclosed in U.S. Pat. application Ser. No. 368,037, filed on June 7, 1973, and matured into U.S. Pat. No. 3,859,983 on Jan. 14, 1975. With a needle disposed approximately as is illustrated in FIG. 3, and with the lower end of the guide placed over an area requiring treatment, an operator, or physician, may tap the end 43 of the needle, as with a finger, to imbed the needle in the patient's body to a desired depth. The guide assembly may then be withdrawn from the needle to leave the needle in the desired position.

It is desired that the needles be restrained from undesired movement longitudinally of the tube, and further that adequate electrical contact be made between the needle and the tube to establish an adequate electrical circuit where desired. In prior practice, when the needle was inserted the tube was removed, and if electrical therapy was desired, an electrical connection had to be made with the needle. With the present device, electrical contact is already available, if desired, when the needle is applied.

SUMMARY OF INVENTION

Invention resides in employing a tubular needle guide to be secured and carried by a handle, and providing on said needle guide a yieldably resistant restraint to engage a needle firmly against interior surface of the side wall of the tubular conductor, to resist undesired movement of the needle in the tubular guide, and to establish an adequate electrical contact of the needle with the tubular guide.

This invention is achieved by the construction hereinafter described and illustrated in the accompanying drawings, wherein:

FIG. 1 is a schematic view showing in small scale, and without detail, a hand-held, electrical locating device connected by a wire to a meter, through which meter the electrical probe is in circuit with an electrode, preferably of a bracelet type.

FIG. 2 is a side elevational view of the electrical locator on a substantially larger scale than FIG. 1.

FIG. 3 is a partial, sectional, vertical elevational view of one end portion of said electrical locator.

FIG. 4 is a top view of a bracelet-type electrode.

FIG. 5 is a side elevational view of said bracelet electrode taken on line 5—5 of FIG. 4.

FIG. 6 is a horizontal, partial, sectional view of said electrode taken on line 6—6 of FIG. 5.

FIG. 7 is a vertical, sectional view taken on line 7—7 of FIG. 2.

FIG. 8 is a vertical, elevational view of the upper portion of the tubular guide and needle, showing a modification of the applied yieldably resistant wire.

FIG. 9 is a partial plan view taken on line 9—9 of FIG. 7.

In these views the reference character 1 designates a manually employable electrode assembly, in circuit with a meter generally designated as 2, and intended to provide (either through batteries or by a transformer, not shown) direct electrical current to be transmitted to and through a patient. The meter is provided with an off-on switch 3, and a control 4 of a conventional type, to regulate the flow of current. There is also provided a calibrated dial 5 and the usual conventional gage arm 6. The meter, of course, would be provided with a means of evaluating a characteristic of electrical current, preferably resistance, which will change when current passes through areas of the body which are less conductive than normal areas, and which evaluation would indicate the possible beneficial application of an acupuncture needle.

The reference character 7 designates an electrode, desirably of the bracelet type, so that the same need not be grasped in the hand of a human patient, because the adequacy of electrical contact may vary with the variations in the grip of a patient, and produce misreadings on the meter.

Referring now to FIGS. 2, 3, and 4, which are of a larger scale than FIG. 1, the reference character 8 designates a handle, of electrically non-conductive material, and formed at one end portion thereof with a diametrically transverse hole 9. A tubular needle guide 10 is received in said hole 9, and carries at one end a wire restraint 12 having an end portion 12a bent to extend freely and resiliently across the upper end of the tubular guide. A hole 11 extends longitudinally through the needle guide to give it the aforesaid tubular character.

An elongated tubular sleeve 13 is received in a hole 14 elongated in the handle, and preferably concentrically therewith. Said hole intersects the aforesaid hole 9, and the sleeve is adapted to receive a coil expansion spring 15 which reacts between a metallic ball 16 and a metallic pin 17, the latter being received diametrically through the walls of said sleeve 13. The spring 15 and the ball 16, pin 17, and the sleeve 13 are all electrically conductive.

To resist withdrawal of the sleeve 13 from the handle 8, it is desired to drill and tap a hole in the handle to receive a set screw 18. To avert the possibility of the set screw conducting electricity to the hand of an operator of the device, it is desired to fill the hole 18 with a wax filler or some other electrically non-conductive substance, 19. It is also desirable to form a slot 20 in an end of the sleeve 13. This affords the use of solder 21 to secure an end portion of a wire 22 disposed in the end portion of said sleeve 13. The wire shown is of the single strand type, and has insulation 23.

A screw 24 is threadedly received in the end portion of the handle 8, so that the end of said screw may bear against the needle guide 10 to positively prevent dislodgment of the needle guide. It is intended that the needle guide have sliding adjustable travel in the hole 9, so that the portion protruding beneath the handle may be adjusted to suit the purposes and convenience of the operator of the device, and such sliding adjustment is available upon loosening of the screw 24 so that it does not engage tightly against the surface of the guide 10. To maintain the guide in the desired position until the screw can be tightened, is the function of the steel ball 16 and spring 15. As is best seen in FIG. 3, it may be desirable to crimp the end 13a of the sleeve 13 to resist the escape of the ball 16 should the guide 10 be withdrawn, to replace it with either a longer or shorter guide. A lock nut 25 may be employed to resist undesired rotation of the screw 24.

A cup 26 is formed by an annular wall 27, and has a bottom wall 28. As may be clearly seen from FIGS. 2 and 3, the shank of the screw 24 passes through the bottom wall to engage in the handle, and the head 24a of the screw clamps the bottom wall against the nut 25. It is desirable that the diameter of the chamber be several times the diameter of the tubular guide, and it is also desirable that said chamber, which is of non-conductive material, be filled with an absorbent material and soaked with a saline solution or alcohol, or the like, to serve as a conductor of electrical current.

The electrical wire 22, 23, extends from the handle to make an appropriate electrical connection (not shown) within the meter. From the opposite side of the meter a wire 38, 39 leads to a bracelet-type of electrode designated generally in FIGS. 5 and 6, as 30. The bracelet portion of the electrode is designated as 31, and the ends of the bracelet are connected between two conductive metal plates 32 and 33. Screws 34 extend through holes in the flattened end plates 35 of the bracelet to maintain the bracelet and said plates in said assembly. The two plates 32, 33 are formed with a groove, respectively designated as 36 and 37 in the respective lower and upper plates, and this groove is dimensioned to clamp on the insulation 39 of the wire 38. It is proposed that the wire 38 be extended beyond the insulation so that it will be engaged with the conductive surfaces of the plates 32, 33. If desired, a soldered connection may also be employed. A conventional expansion strap is contemplated, but, of course, any strap that will grip a limb of a patient, human or animal, will serve.

It may now be seen that by engaging a bracelet electrode on the wrist of a patient or the limb of an animal, and by tracing either the cotton-filled chamber 26 or the tubular electrode 10 over the skin over areas suspected of requiring treatment, the current will pass from the meter through one electrode or the other, and thence through the body of a patient to the other electrode and then back to the meter where the dial gage 5 will indicate resistance. Clearly the area can at first be generally located by the larger diameter chamber 26, and the specific area, should it be a small one, may be narrowed down by subsequent use of the tubular guide. Once the precise area has been determined, a needle 42, having a sharply pointed end may be dropped into the guide, and tapped in position in the body of a patient without first having to remove the locator and provide some form of marking or indentation of the skin for a later application of the needle after the locating device has been removed.

Obviously, it may require a medically skilled person to be aware of areas of the body where additional resistance might normally be anticipated, and which would therefore not normally require or benefit from treatment.

It should be noted that the needle 42 is formed with a shank 43, of greater diameter than the needle itself. It frequently occurs that a needle is tapped into position by a finger tip of the operator, and the shank 43 affords a surface which may be tapped.

As may be seen clearly in FIGS. 3, 7, and 9, the end portion 12a of the coil spring 12 is disposed across the end of the tubular guide 10 so as to engage the needle 42 with the side wall of said tubular guide. It is proposed to use a spring 12 of adequate resilience that the end portion 12a may be yieldably forced to move and permit passage of the needle shank 43. It is believed clear that the restraint 12a releasably restrains the needle in a desired position, but permits ready adjustment of said position. It also, as is desired for this invention, engages the needle against the wall of the tubular guide with sufficient firmness to make an adequate electrical contact therewith.

In FIG. 8, a modified version of the invention has a rectilinear length 41 of spring wire secured to the outer wall of the tubular guide, as by silver soldering, or the like. Downwardly said wire terminates in an arcuate section 41b, also secured to said outer wall. The yieldably resistant end portion of such wire, extending across an open end of the tube, is designated 41a.

What I claim is:

1. A guide assembly for an acupuncture needle, including
    a tubular guide to receive and guide an acupuncture needle,
    said tubular guide having both ends open, and
    a yieldably resilient restraint carried by said tubular guide,
    and having a section extending substantially transversely across an open end thereof to form an opening between the interior surface of the guide and the section, said section being adapted to yieldably engage a needle against the interior surface of said guide to frictionally resist undesired movement of such needle longitudinally of said tubular guide.

2. A guide assembly for an acupuncture needle as set forth in claim 1,
    said restraint having a portion elongated downwardly and exteriorly of said tubular needle guide, and being rigidly secured thereto.

3. A guide assembly for an acupuncture needle, as set forth in claim 2,
    said restraint including a coil spring rigidly received and secured upon an end portion of said tubular guide,
    said coil spring having an end portion thereof bent to extend across the end of said tubular guide to form said section, and
    said end portion being so disposed across said end of said guide as to yieldably engage a needle in said guide.

4. A guide assembly for an acupuncture needle, including
    a tubular guide to receive and guide an acupuncture needle, said tubular guide having both ends open,
    a yieldably resilient restraint carried by said tubular guide, and extending across an open end thereof, to yieldably engage a needle in said guide and frictionally resist undesired movement of such needle longitudinally of said tubular guide, and
    an elongated handle adapted to carry said tubular guide,
    said tubular guide having sliding travel in said handle for adjustment to desired positions relative to said handle, and a first hole extending through said handle transversely of its longitudinal axis, and said tubular guide being slidably received in said first hole.

5. The combination as set forth in claim 4,
    said handle further having a second hole elongated longitudinally thereof, and said second hole intersecting said first hole, a first means disposed within said second hole to react against said tubular guide to yieldably resist undesired adjustable travel of said guide.

6. The combination as set forth in claim 5, a second means carried by said handle and adapted thereof for releasable engagement, with said tubular guide to restrain said guide from travel.

* * * * *